United States Patent
Kram

(10) Patent No.: US 7,615,371 B2
(45) Date of Patent: Nov. 10, 2009

(54) METHOD AND APPARATUS FOR TREATING A BIOLOGICAL SAMPLE WITH A LIQUID REAGENT

(75) Inventor: Brian H. Kram, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 578 days.

(21) Appl. No.: 11/016,407

(22) Filed: Dec. 17, 2004

(65) Prior Publication Data

US 2005/0164374 A1     Jul. 28, 2005

Related U.S. Application Data

(60) Provisional application No. 60/532,063, filed on Dec. 23, 2003.

(51) Int. Cl.
*C12M 1/34* (2006.01)
*C12M 3/00* (2006.01)

(52) U.S. Cl. .................... 435/287.9; 435/287.5
(58) Field of Classification Search .............. 435/287.9
See application file for complete search history.

(56) References Cited

U.S. PATENT DOCUMENTS

| | | |
|---|---|---|
| 3,667,896 A | 6/1972 | McCormick et al. ............. 8/3 |
| 3,871,895 A | 3/1975 | Adler ............................ 117/3 |
| 3,977,568 A | 8/1976 | Smith |
| 3,979,576 A | 9/1976 | Janson |
| 4,043,292 A | 8/1977 | Rogers et al. |
| 4,092,952 A | 6/1978 | Wilkie et al. |
| 4,120,262 A | 10/1978 | Adler et al. ................. 118/642 |
| 4,296,069 A | 10/1981 | Smith et al. |
| 4,358,470 A | 11/1982 | Rasmussen |
| 4,384,193 A | 5/1983 | Kledzik et al. |
| 4,430,299 A | 2/1984 | Horne |
| 4,543,236 A | 9/1985 | von Gise |
| 4,629,862 A | 12/1986 | Kitagawa et al. |
| 4,635,791 A | 1/1987 | Jackson et al. |
| 4,847,208 A | 7/1989 | Bogen |
| 4,858,155 A | 8/1989 | Okawa et al. |
| 4,865,986 A | 9/1989 | Coy et al. |
| 4,985,206 A | 1/1991 | Bowman et al. |
| 5,075,079 A | 12/1991 | Kerr et al. |

(Continued)

FOREIGN PATENT DOCUMENTS

EP     0 201 780     11/1986

(Continued)

OTHER PUBLICATIONS

EPO Office Action for Application No. 04 814 993.4—1234, dated Oct. 8, 2007.

(Continued)

*Primary Examiner*—Walter D Griffin
*Assistant Examiner*—Lydia Edwards
(74) *Attorney, Agent, or Firm*—Hayes Soloway P.C.

(57) ABSTRACT

A method and apparatus for treating a biological sample with a liquid reagent, comprising first and second substrates having facing surfaces defining a space therebetween in which the biological sample may be treated with the liquid reagent, wherein the first substrate comprises a relatively rigid fluid impermeable element while the second substrate comprises a relatively flexible liquid impermeable element.

40 Claims, 13 Drawing Sheets

U.S. PATENT DOCUMENTS

| | | | |
|---|---|---|---|
| 5,105,066 | A | 4/1992 | Houdy et al. |
| 5,154,889 | A | 10/1992 | Muraishi |
| 5,207,987 | A | 5/1993 | Kureshy et al. |
| 5,280,156 | A | 1/1994 | Niori et al. |
| 5,316,452 | A | 5/1994 | Bogen et al. |
| 5,364,790 | A * | 11/1994 | Atwood et al. ............ 435/287.2 |
| 5,425,918 | A | 6/1995 | Healey et al. |
| 5,496,518 | A | 3/1996 | Arai et al. |
| 5,523,056 | A | 6/1996 | Miller |
| 5,589,649 | A | 12/1996 | Brinker et al. |
| 5,595,707 | A | 1/1997 | Copeland et al. ............... 422/64 |
| 5,601,141 | A | 2/1997 | Gordon et al. |
| 5,654,200 | A | 8/1997 | Copeland et al. |
| 5,675,715 | A | 10/1997 | Bernstein et al. .............. 395/82 |
| 5,681,529 | A * | 10/1997 | Taguchi et al. ................. 422/61 |
| 5,681,741 | A * | 10/1997 | Atwood et al. ............ 435/287.2 |
| 5,696,887 | A | 12/1997 | Bernstein et al. .............. 395/82 |
| 5,839,091 | A | 11/1998 | Rhett et al. |
| 5,922,604 | A | 7/1999 | Stapleton et al. ............... 436/46 |
| 5,947,164 | A | 9/1999 | Bogen et al. |
| 5,947,167 | A | 9/1999 | Bogen et al. |
| 5,958,341 | A | 9/1999 | Chu ............................ 422/99 |
| 6,050,719 | A | 4/2000 | Winkler et al. ............... 366/144 |
| 6,092,695 | A | 7/2000 | Leoffler |
| 6,096,271 | A | 8/2000 | Bogen et al. |
| 6,114,122 | A | 9/2000 | Besemer et al. ................. 435/6 |
| 6,168,948 | B1 | 1/2001 | Anderson et al. ............ 435/287 |
| 6,180,061 | B1 | 1/2001 | Bogen et al. |
| 6,183,693 | B1 | 2/2001 | Bogen et al. |
| 6,218,191 | B1 | 4/2001 | Palander ...................... 436/63 |
| 6,296,809 | B1 | 10/2001 | Richards et al. ................ 422/64 |
| 6,420,114 | B1 | 7/2002 | Bedilion et al. ................. 435/6 |
| 6,458,526 | B1 | 10/2002 | Schembri et al. ................ 435/4 |
| 6,485,918 | B1 | 11/2002 | Schermer et al. ................ 435/6 |
| 6,495,106 | B1 | 12/2002 | Kalra et al. |
| 6,541,261 | B1 | 4/2003 | Bogen et al. |
| 6,569,674 | B1 | 5/2003 | McGarry et al. ............ 435/287 |
| 6,582,962 | B1 | 6/2003 | Richards et al. |
| 6,673,620 | B1 | 1/2004 | Loeffler et al. |
| 6,783,733 | B2 | 8/2004 | Bogen et al. |
| 6,827,900 | B2 | 12/2004 | Thiem et al. |
| 2002/0054830 | A1 | 5/2002 | Bogen et al. |
| 2003/0190744 | A1 | 10/2003 | McGarry et al. |
| 2004/0191128 | A1 | 9/2004 | Bogen et al. |
| 2004/0241050 | A1 | 12/2004 | Bogen et al. |
| 2005/0098032 | A1* | 5/2005 | Tsai .............................. 95/46 |

FOREIGN PATENT DOCUMENTS

| | | |
|---|---|---|
| EP | 0 611 598 A2 | 8/1994 |
| GB | 1562643 | 3/1980 |
| WO | WO 93/09486 | 5/1993 |
| WO | WO 03/091137 A2 | 11/2003 |

OTHER PUBLICATIONS

"The Complete Innunoperoxidase System," Immulok, advertisement, 1 pg.

United States Court of Appeals for the Federal Court, *Cytologix Corporation* v. *Ventana Medical Systems, Inc.*, Case No. 04-1446, Decision decided Sep. 21, 2005, pp. 1-18.

\* cited by examiner

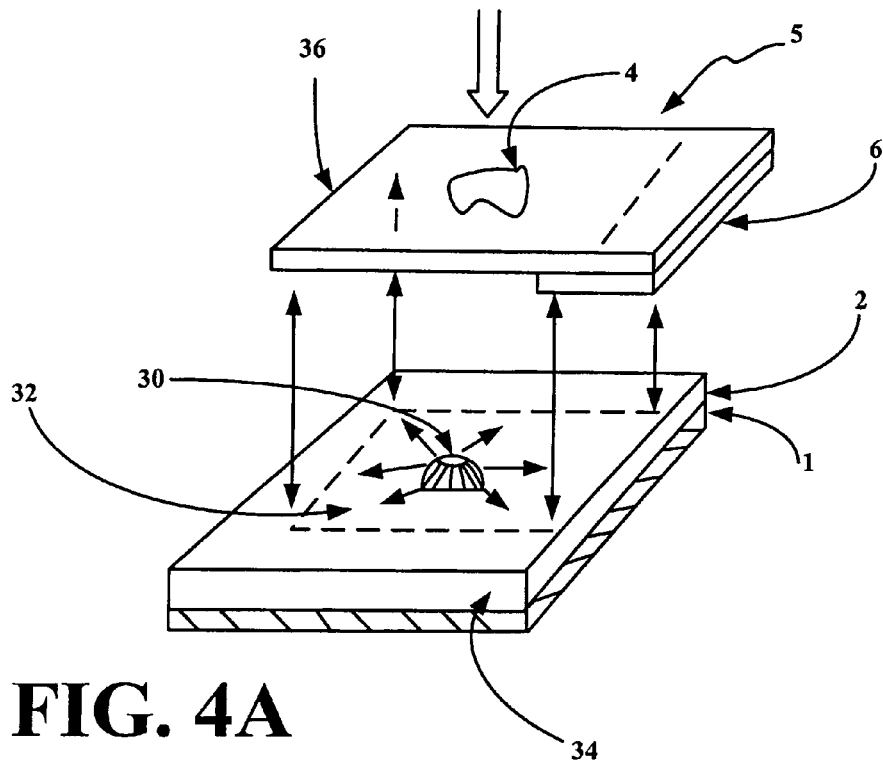
FIG. 4A
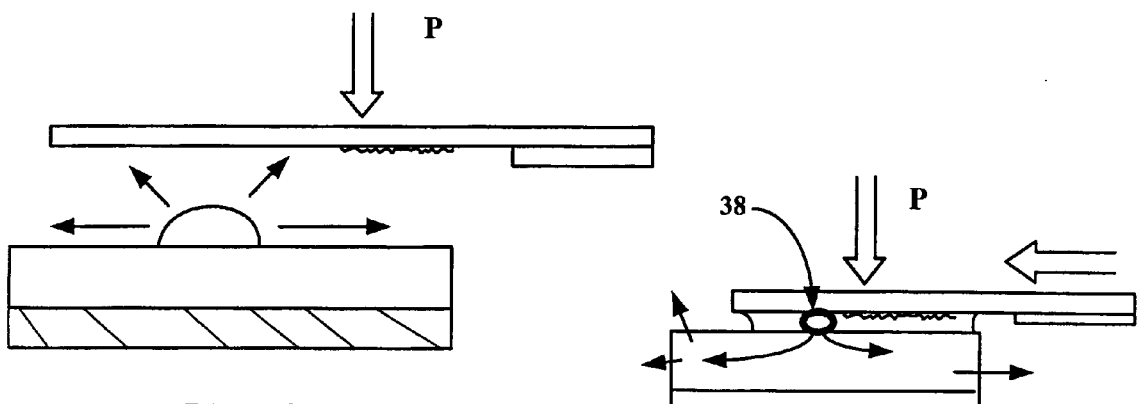
FIG. 4B
FIG. 4C

HYDROPHOBIC VS.
HYDROPHILIC SURFACES

METHOD AND APPARATUS FOR TREATING A BIOLOGICAL SAMPLE WITH A LIQUID REAGENT

CROSS REFERENCE TO RELATED APPLICATIONS

This application claims priority from U.S. Provisional Application Ser. No. 60/532,063, filed Dec. 23, 2003.

BACKGROUND OF THE INVENTION

1. Field of the Invention

This invention relates to methods and apparatus useful in the fluid treatment of surfaces. It has further utility in the minimization of fluid consumables by spreading of a treatment fluid into a thin film specific to a designated treatment zone. The invention has particular utility in connection with the fluid treatment of flat substrates and more specifically staining of biological tissue samples on glass slides and will be described in connection with such utility, although other utilities are contemplated.

2. Description of Related Art

The analysis of biological tissue samples is a valuable diagnostic tool used by the pathologist to diagnose many illnesses and by the medical researcher to obtain information about a cell structure.

In order to obtain information from a biological tissue sample it usually is necessary to perform a number of preliminary operations to prepare the sample for analysis. While there are many variations of the procedures to prepare tissue samples for testing, these variations may be considered refinements to adapt the process for individual tissues or because a particular technique is better suited to identify a specific chemical substance or enzyme within the tissue sample. However the basic preparation techniques essentially are the same. Biological tissue samples may derive from solid tissue such as from a tissue biopsy or may derive from liquid based preparations of cellular suspensions such as from a smear (e.g., PAP smear).

Typically such procedures may include the processing of the tissue by fixation, dehydration, infiltration and embedding; mounting of the tissue on a glass slide and then staining the sample; labeling of the tissue through the detection of various constituents; grid analysis of tissue sections, e.g., by an electron microscope, or the growing of sample cells in culture dishes.

Depending on the analysis or testing to be done, a sample may have to undergo a number of preliminary steps or treatments or procedures before it is ready to be analyzed for its informational content. Typically the procedures are complex and time consuming, involving several tightly sequenced steps often utilizing expensive and toxic materials.

For example, a typical tissue sample may undergo an optical microscopic examination so that the relationship of various cells to each other may be determined or abnormalities may be uncovered. Thus, the tissue sample must be an extremely thin strip of tissue so that light may be transmitted therethrough. The average thickness of the tissue sample or slice (often referred to as sections) is in the order of 2 to 10 micrometers (1 micrometer=1/1000th of a millimeter). Typically, a tissue sample is either frozen or fixed in a material (a fixative) which not only preserves the cellular structure but also stops any further enzymic action which could result in the putrification or autolysis of the tissue.

After fixation, the tissue sample is then dehydrated by the removal of water from the sample through the use of increasing strengths of alcohol. The alcohol then is replaced by a chemical which mixes with wax or some other plastic substance impregnant which can permeate the tissue sample and give it a consistency suitable for the preparation of thin sections without disintegration or splitting.

A microtome is then utilized to cut thin slices from the tissue sample. The slices may be on the order of 5 to 6 micrometers thick while the diameter may be on the order of 5000 to 20000 microns long. The cut thin sections are floated on water to spread or flatten the section. The section is then disposed on a glass slide usually measuring about 8 by 2.5 centimeters (1×3 inches).

The wax or other impregnant is then removed by exposing the sample to a solvent, the solvent removed by alcohol, and the alcohol removed by decreasing the alcoholic concentrations until eventually the tissue is once more infiltrated by water. The infiltration of the sample by water permits the staining of the cell constituents by water soluble dyes.

Prior to the development of automated procedures for the preparation of tissue samples, it often took from two to ten days before the tissue could be examined under a microscope. In more recent years automated processes have been developed utilizing apparatus to transfer the sample from one fluid to another at defined intervals, and as a result the preparation time has been significantly reduced to 12 to 36 hours.

The foregoing discussion of the prior art derives largely from U.S. Pat. No. 5,675,715 to Bernstein et al. which describes an automated system for performing a plurality of independent analysis procedures simultaneously comprising a robotic arm which moves different tissue samples along a plurality of processing stations arranged along x and y coordinates wherein the tissue samples are subjected to various processes. See also U.S. Pat. No. 5,595,707 to Copeland et al., which describes an automated slide processing system comprising a reagent carousel cooperating with a sample support carousel to supply a sequence of preselected reagents to each of the samples with interposed mixing, incubating and rinsing steps cooperating therewith. Apparatus made in accordance with U.S. Pat. No. 5,675,715 and 5,595,707 and others is available commercially from Ventana Medical Systems, Inc. of Tucson, Ariz., and has achieved substantial commercial success and significantly reduced the time and cost of testing biological samples.

A biological tissue sample is finally viewed by a pathologist in an as-mounted state on a glass slide. Much of the processing of biological specimens, therefore, is adapted to the sequential application and removal of multiple fluids to an essentially two dimensional treatment zone on a 1"×3" glass slide format.

SUMMARY OF THE INVENTION

The present invention provides improvements over the foregoing and other prior art by permitting a reduction in the amount of fluid volume necessary to conduct desired biological reactions. Reducing the fluid volume of reactants results in cost savings of reagents and also results in a reduction in the amount of rinse fluids necessary which in turn means a reduction in the amount of waste materials that need to be disposed of. Fluid volume reduction further results in less fluidic management complexity which in turn ultimately permits greater process reliability. It also permits the reduction or elimination of fluid waste disposal.

The present invention further provides improvements by permitting a reduction in processing time to treat biological specimens. Reductions in fluidic requirements permits rapid treatments and their sequencing which in turn permits greater throughput and/or sample turn around time. The present invention further provides that one or more treatments surprisingly do not require any rinsing per se, further permitting the reduction of fluidic volume requirements and processing time.

The present invention provides a system, i.e., method and apparatus for managing micro volumes of fluid. The invention in one aspect provides methods and apparatus for minimizing fluid volume requirements and processing times for performing staining or biological reactions by creating a staining or reaction chamber formed between a slide and an opposed element such as a hydrophobic element. More particularly, the invention provides a method and apparatus for spreading a small fluid volume across a slide surface while providing a regulated passive escape of trapped gas bubbles and simultaneously avoiding significant evaporative loss.

In a preferred embodiment of the invention a slide is conveyed at an angle to the opposed element to discourage gas bubble entrapment.

The invention is directed to an apparatus having a treatment zone for treating a biological sample with a liquid reagent, comprising first and second substrates having facing surfaces defining a space therebetween in which said biological sample may be treated with the liquid reagent, wherein the first substrate comprises a relatively fluid impermeable element while the second substrate comprises a relatively flexible gas permeable element.

The invention is also directed to a method for treating a biological sample with a liquid reagent comprising the steps of providing a sample and the liquid reagent in the space defined between facing surfaces, and pressing the surfaces together to reduce the space therebetween and expel gas trapped therebetween.

The invention is further directed to an apparatus for treating a biological sample with a liquid reagent comprising first and second substrates having facing surfaces defining a space therebetween in which the biological sample may be treated with the liquid reagent in a treatment zone, wherein the first substrate comprises a relatively fluid impermeable element while the second substrate comprises a gas permeable element, the apparatus further including a device for separating the first and second substrates downstream of the treatment zone.

The invention is also directed to a method for treating a biological sample with a liquid reagent comprising the steps of providing the preceding apparatus for treating the biological sample, providing the sample in liquid reagent in the space defined between the facing surfaces, pressing the substrates together to reduce the space therebetween and expel gas trapped therebetween and separating said substrates.

BRIEF DESCRIPTION OF THE DRAWINGS

Yet other features of the present invention will be seen from the following detailed description taken in conjunction with the accompanying drawings wherein:

FIGS. 4a-4c illustrate schematically and FIG. 7 illustrates a cross-sectional view of one preferred embodiment of the present invention;

DETAILED DESCRIPTION OF THE INVENTION

Before considering the present invention in detail, a review of the phenomenon of wetting and spreadability would be useful for a proper understanding of the present invention.

Figure 1:
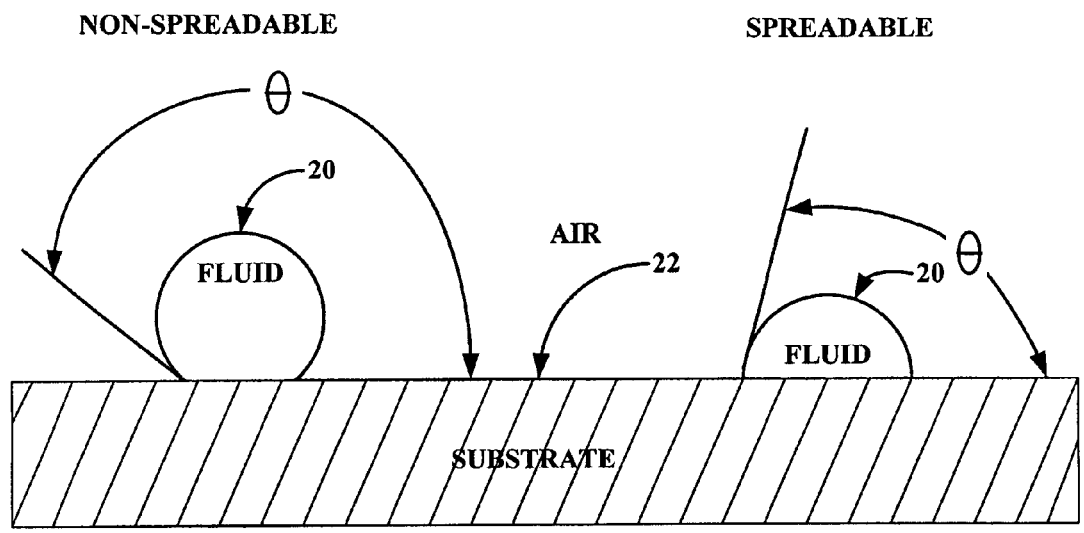
FIG. 1 compares wetting and non-wetting of a surface by a fluid droplet in accordance with the prior art.

Spreadability refers to the relationship of a fluid on a surface. There is a balance of forces that determine whether or not a fluid has a tendency to spread with respect to said surface:

i) fluid-fluid interaction (tension)
   ii) fluid-surface interaction
   iii) environment (usually air) interaction with fluid and surface Referring to FIG. 1, consider a fluid droplet 20 resting on a horizontal surface 22. Absent other forces, the fluid droplet, in an effort to minimize its surface would be drawn into a sphere due to its surface tension. In other words, when fluid-fluid forces dominate, fluid interacts more strongly with itself rather than the surface. By way of example, and as applied to aqueous ($H_2O$) based systems, hydrogen bonding in $H_2O$ based fluids is sufficiently strong such that in many circumstances aqueous fluids will potentially interact fluid-fluid rather than fluid-surface; e.g., when a surface exhibits relatively low interaction with the fluid, i.e., the surface is "hydrophobic", if the fluid is de-ionized $H_2O$. The fluid will tend to "ball up" on the surface and readily can be destabilized, e.g., can be made to roll off of the surface with modest agitation. However, gravity and interfacial tensions between the liquid droplet and its surroundings usually act against this surface tension so that the liquid droplet assumes other shapes. Hydrophilic surfaces are those wherein the aqueous-based fluid-surface interaction is significant. When fluid-surface interaction forces are strong, fluid will preferentially contact the surface and thereby spread out on the surface.

Contact angle indicates this balance of forces. A contact angle greater than 90 degrees indicates relatively weak fluid-surface interaction forces; a contact angle less than 90 degrees indicates relatively strong fluid-surface interaction and spreadable condition. Surface "wettability" is defined as strong fluid-surface interaction with tendency for fluid spreading.

In a spreadable condition, the fluid will tend to spread. This is a thermodynamic condition. It may not spread, or spreading may be constrained or mediated over time due to kinetic limitations. Using an opposing contacting surface, a fluid can be made to spread very rapidly allowing the thermodynamic state to be satisfied. The contacting surface may or may not be spreadable with respect to the fluid. With a fluid between two opposing surfaces, only one surface needs to be interactive with the fluid such that it spreads. Thus, in the case of a surface wettable by the liquid, the fluid droplet 20 spreads along the surface 22. The angle θ formed between the fluid and solid is called the dihedral angle or contact angle. In the case of total wetting θ equals 0°. In the process of spreading however, gas pockets may inadvertently become entrained and entrapped within the resulting fluid layer. The present invention, in part, provides a solution for resolving entrained or entrapped gas pockets.

Figure 2A:
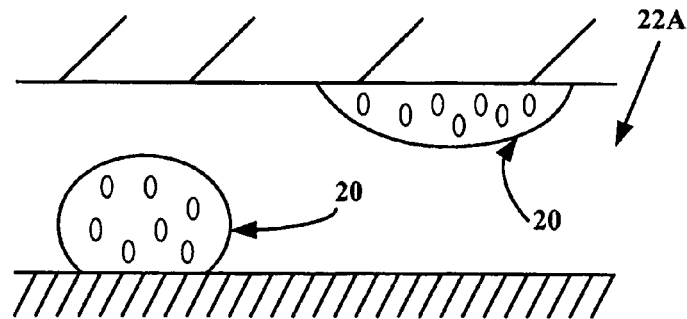
FIGS. 2a-2c illustrate fluid droplet behavior of wetting and non-wetting of fluids placed between two surfaces in accordance with the prior art.
Figure 2B:
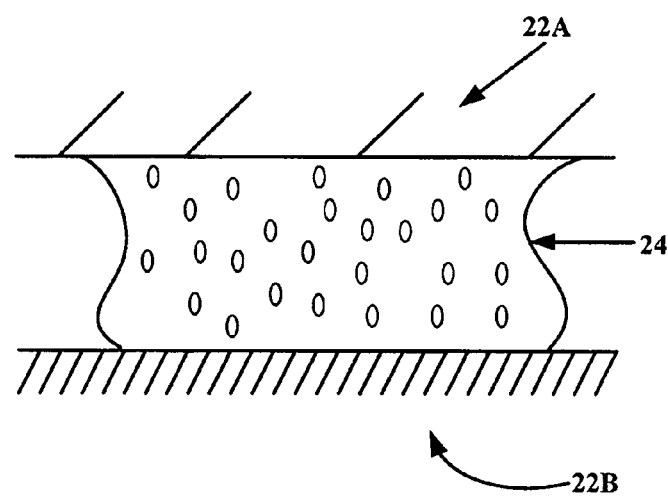
Figure 2C:
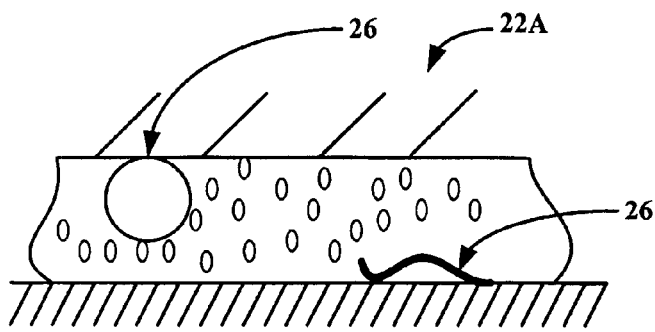
Figure 3:
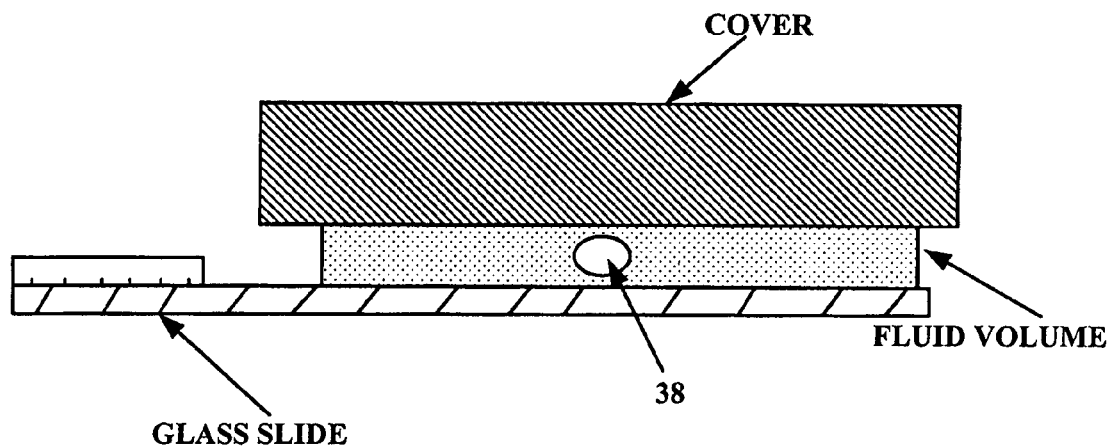
FIG. 3 illustrates vapor lock problems common when a fluid is placed between two surfaces in accordance with the prior art.

FIGS. 2a-2c and FIG. 3 illustrate what happens when a slide and a substrate in accordance with the prior art, with wetting and non-wetting fluid-surfaces, are brought together. Referring in particular to FIGS. 2a-2c, as the surfaces 22a and 22b are brought closer together, initially the fluid droplets 20 join to form a larger fluid body 24. As fluid spreads within the interfacial gap between the surfaces 22a and 22b, one or more gas pockets 26 may become entrapped as the fluid body assumes a thin fluid film shape. If the fluid volume is sufficient, essentially all the space directly between the two opposed surfaces will fill with fluid and assume that shape. Some portions of that shape may fill before others and connect with other advancing fluid portions. In this manner, slower portions may never have a chance to wet because they become encircled by advancing portions and thus become "vapor locked" with a pocket of associated gas. Alternatively, gas pockets may form, post spreading, from dissolved gases coming out of a saturated solution due to changes in local pressure and/or temperature.

Treatment fluids especially when small in volume need somehow to be reliably administered across a complete treatment area and spatially managed there. For example, for the staining of biological specimens placed onto a 1"×3" microscope slide, fluids need to be first placed and then removed from a rectangularly shaped flat surface. As discussed above, small fluid volumes tend to remain in droplet formation to minimize thermodynamically driven surface tension forces between liquids and atmosphere. As a result, fluid spreadability across a surface—especially when fluid volumes may be minimal—can be a real challenge. For instance, fluids may sit on a surface as droplets rather than a continuous thin film. Flooding a surface is one method to resolve this problem; however, flooding entails the use of a large volume of fluid which is not economical and also requires the management of large reservoirs, waste systems, and complex plumbing. Additional volume also is needed to fill the rectangular shape of the slide at the corners. One simple approach to solving these fluid dynamic challenges is to simply immerse the entire substrate or the treatment section of the substrate into a body of fluid. Early treatment methods as well as some conventional manual methods have exploited this "bucket chemistry" approach. However, the contemporary state of the art has successfully exploited "fluids on a slide" approach to great effect, especially in regards to automation of fluidic treatments. In this approach, unless a large flooded volume approach is used (e.g., as in apparatus available from DAKO Cytomation AS, Copenhagen, Denmark), some means of enchambering is employed to better manage (minimize and control) fluidic volumes on the slide. Previous prior art methods strive for precise volume control, and in some cases with volume minimization in mind (hybridization processes because of reagent cost), have employed various forms of enchambering (e.g., LIQUID COVERSLIP™—Ventana Medical Systems, Inc., Tucson, Ariz.; slide chambers—Cytologix Corporation, Cambridge, Mass.; chamber walls—Agilent Technologies, Inc., Palo Alto, Calif.; chamber walls—Amersham Biosciences, Piscataway, N.J.; TechMate™ capillary glass slides—Biotek Solutions, Inc., Santa Barbara, Calif.). Conventionally, seals of one sort or another are used to control on-slide volumes via fixed chamber boundaries. Providing a "liquid tight" chamber further allows pressurization of the fluids as well as in some instances mechanical motion of the walls providing fluid transport to and from the chamber and/or mixing.

However, the need to both contain and specifically place a fluid with respect to a substrate presents various technical challenges and problems. Sealing means entail specific and precise coupling of elements that are generally encumbering to a process. Two opposing elements with a mediating seal generally require precise alignment and attention to proper maintenance (e.g., cleanliness) of the critical surfaces. Seals are subject to defect and failure. For example, a seal involving a mediating O-ring (or gasket) captured between 2 surfaces may be compromised by a defect in the O-ring, a twist in the O-ring, or contaminant particles on any of the critical mating surfaces. In another example, a seal involving an adhesive may be compromised by defects in the adhesive, voids in the adhesive, or contaminant particles. Also, sealing is generally performed directly to the substrate itself. The sealing quality of incoming substrates with different processes with various customers may be a significant variable difficult to manage for a robust seal-dependent process. The present invention addresses the foregoing and other technical problems while also solving the important issue of entrapped bubbles within the fluid thin film without resort to sealing means while also avoiding significant evaporative loss. In the present invention, the chamber "sides" are not physically bounded and the opposing substrate surfaces may be either fixed or allowed to float with respect to one another.

Figure 5:
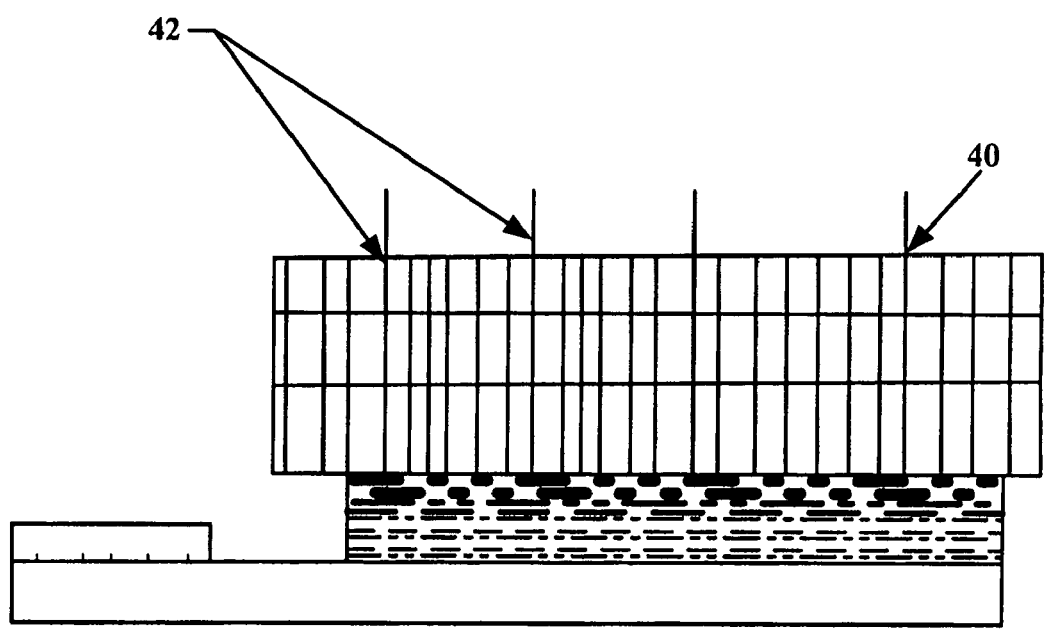
FIGS. 5, 6a and 6b are views similar to FIG. 7, and illustrate alternative embodiments of the present invention.
Figure 6A:
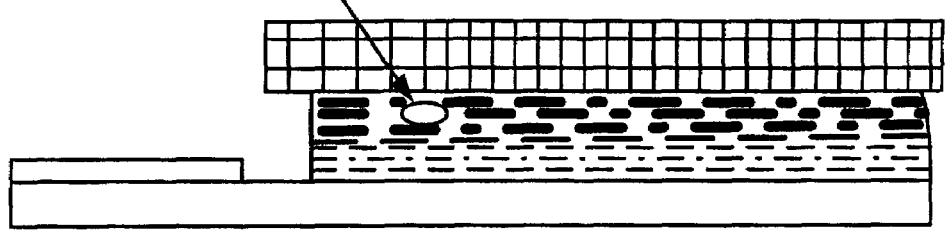
Figure 6B:
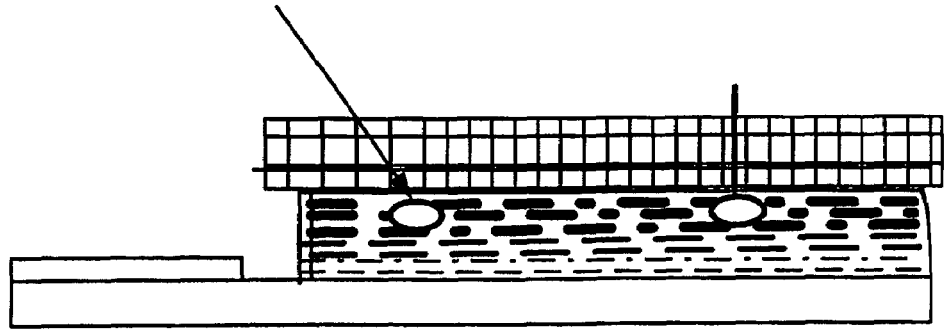

The present invention is used for advantageously performing staining or biological reactions of biological samples on slides. Referring to FIGS. 4a-4c, 5, 6a and 6b the principle of operation is as follows. An aqueous based fluid droplet 30 can be spread as a thin layer 32 when placed between two surfaces 34, 36. If both surfaces are hydrophilic, surface interactions will contribute to liquid spreading. However, gas pockets 38 (see FIG. 3) may form in the gap between the two surfaces during fluid spreading or after spreading due to dissolved gases coming out of solution. If both surfaces are non-permeable to gas (e.g., glass), any trapped or formative gas pockets essentially become fixed in location disrupting continuity of the liquid layer (otherwise described as a condition of "vapor lock"). Liquid tension forces are inhibited from collapsing the gas bubble by the exerted vapor pressure of the gas bubble. In other words, there is no place for the gas to go. Further, viscous forces dominate in thin capillary geometries such that the gas bubbles 38 can be exceedingly difficult to dislodge. Referring in particular to FIGS. 4c and 5, the use of a gas permeable material 40 as one of the surfaces in accordance with the present invention provides passages 42 for escape of the gas under the influence of liquid tension forces. Surface properties are important because if the surface of the gas permeable material 40 strongly interacts with the liquid, liquid will be absorbed, blocking access to the permeable element, and the bubble remains trapped between the two liquid-coated surfaces as illustrated in FIG. 6a. On the other hand, if the surface is largely non-interactive with the liquid, no blocking occurs and the gas bubble is effectively expelled by the driving force (which is passive) of the liquid tension as illustrated in FIG. 6b. Favoring this process is low spreadability of the fluid at this surface; e.g., high surface hydrophobicity and high surface tension of an aqueous-based liquid.

Figure 7:
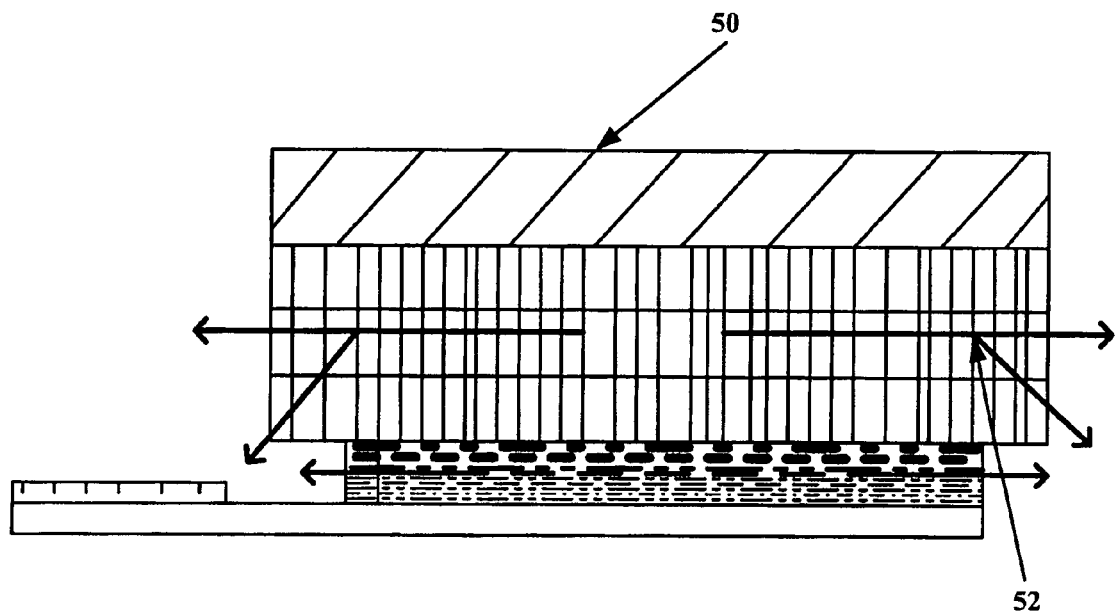

Thus, the present invention in one aspect is based on the provision of a hydrophobic high gas permeable material 40 for forming a boundary surface of an open sided reaction chamber to provide pressure relief for "burping" gas pockets from within a thin liquid film. A microporous hydrophobic material such as Gore-Tex® is preferred for its very high gas permeability. High water entry pressure (WEP) materials are further preferred so as to prevent blow-through of liquid. High water entry pressure can be attained by using small pore sized (0.05 to 200 micron) material, or by using a porous hydrophobic material laminated to a liquid-impermeable backing 50 as illustrated in FIG. 7. A liquid-impermeable backing prevents blow-through of a liquid even if the porous hydrophobic element has large pore sizes (e.g., 200 to 2000 microns). It is preferred that the material 40 present a flat smooth surface for efficient fluid spreading since any surface depressions can result in localized pooling of fluid impacting spreading efficiencies for very low volume applications. Smaller pore size hydrophobic materials (less than~200 microns) provide for a more flat smooth surface. Moreover, any significant warp in the material may result in lack of fluid coverage. It is also preferred that the material 40 is dimensionally stable, but flexible so that it may be manipulated, meaning that it can be slid over surfaces or rolled around rollers, for example.

One presently preferred material 40 is "Plumbers Tape", i.e., Teflon® tape, commonly used on pipe threading to prevent water leakage. Plumbers Tape is useful since it meets the following criteria:

1) It is hydrophobic—comprised of Teflon® (polytetrafluoroethylene);

2) It is microporous—the Teflon® is expanded resulting in microporosity in the range of 0.05 to 5 microns;

3) It has relatively high water entry pressure—it is relatively dense with very small pores;

4) It is flexible and conformable—it can assume the dimensionality (flatness & smoothness) of a backing element or surface; and 5) "Stiction" is high—it tends to grip smooth hard surfaces if pressed onto such surfaces.

Since evaporation across a high surface area permeable material may be high, in order to regulate evaporation, material 40 preferably is backed by a substantially non-permeable material 50. Thus, vapor pressure (and vapor lock relief) between the fluid phase and atmosphere is mediated laterally through the permeable material 40 and restricted to the surface area exposed just at the edges 52 of the article. Preferred as a hydrophobic micro-porous permeable material 50 is 1.5" wide Military Grade Teflon® Thread Tape available from McMaster-Carr Supply Company, Atlanta, Ga., P/N 6802K66 ("Plumber's Tape"), which provides rapid pressure equilibration, backed by a substantially non-permeable flexible membrane or coating. Other suitable porous hydrophobic materials include siliconized paper and porous polypropylene membrane.

FIGS. 4a-4c illustrate in a general way the manner by which a substrate 34, a fluid droplet 30, and a glass specimen slide 36 are brought together in accordance with the present invention. As can be seen, as the glass specimen slide 36 and substrate 34 are brought closer together the liquid droplet 30 begins to spread thinly and uniformly between the opposing surfaces with gas bubbles being effectively expelled at the membrane surface and out through the edges of the article.

Microscope glass slide dimensions are nominally 1"×3" Conventional Superfrost™ slides from Erie Scientific Company, Portsmouth, N.H. which include a 0.75" label region at the end of the slide, leaving approximately 2.25"×1" active area. Some microarray slides use larger active areas and consequently smaller or no label areas. In the present case, an active area of 2"×1"—or 5.0×2.5 cm—is assumed. Actual active areas can be accordingly adjusted upwards or downwards, depending upon application.

A 5.0×2.5 cm area equates to 12.5 cm$^2$. This was the actual test area used for stain processing and characterizing volumetric ranges in the following examples. Using less than the total glass slide area allows for handling of the slide via gripping the label-end. Using less than the total membrane article area allows for handling/gripping of said article.

An applied fluid volume range can be defined wherein practical lower and upper limits are described. This can be defined in terms of per slide basis; however, it is clearer to define in terms of per cm$^2$ basis since the active area may vary as explained above.

At the lower fluid volume end, 0.0007 ml per cm$^2$ with a fluid layer thickness of 7 μm was about as thin as could be fully spread over the entire contact area for a given aqueous-based fluid, glass slide, and given contacting membrane. Spreading did not occur spontaneously but required some work; i.e., the two surfaces required some pressure P to facilitate spreading. Furthermore, it was advantageous to move or oscillate one surface with respect to the other to help "drive" the fluid throughout the gap between the surfaces. At this lower limit, viscous forces of the fluid are significant such that the "flow" of the fluid is retarded. Thus, at the lower volume end additional steps sometimes may be required to move fluid throughout the gap so as to attain thermodynamic equilibrium of a fully wetted contact area. Additionally, at the lower volume end entrapped gas pockets did not seem to readily "burp". Slow burping may very well be associated with high viscous forces retarding the movement/collapse of the entrapped gas-liquid boundary.

Fluid volumes of 0.002 to 0.0055 ml per cm$^2$ (20-55 microns thick fluid layer) were found to be a middle range where volumes could be minimized without incurring severe viscosity issues. Both spreading and burping generally occur spontaneously within this range, the greater the volume, the more spontaneous.

Fluid volumes greater than 0.0055 ml per cm$^2$ up to approximately 0.036 ml per cm$^2$ can also be useful (55 to 360 microns thick layer). Burping and spreading proceed readily. As volumes increase, however, fluids at the boundaries may have a greater tendency to be inadvertently squeezed out of the contact area and pinched off from the main fluid body. Droplets may then end up at the edge or outer surfaces of the slide and/or membrane in an uncontrolled manner. Inadvertent droplet formation thus becomes more sensitive to contacting pressure and its control as volumes increase. Inadvertent droplets may not necessarily be a problem per se, but require some attention as to management.

Furthermore, higher volumes are akin to "floating" one of the substrates over the other—viscous forces no longer appear so dominant. One effect is that the fluid layer can act as a "fluid bearing"; e.g., the top substrate can readily roll off of the bottom substrate with a slight tilt of the apparatus. This property can be exploited for separation of the two substrates post treatment. It also would require fixturing the two substrates to prevent uncontrolled separation during treatment. Conversely, with low volumes, the apparatus can be severely tilted without effecting separation of the two substrates due to the high viscous forces at work.

Thus, any three of these defined volume ranges may be useful, not just the lowest volume regimes. Volume requirements are traded against certain characteristic features that offer specific design possibilities. Higher reagent volumes than currently used may thus be preferred depending upon the preferred design space.

Figure 10A:
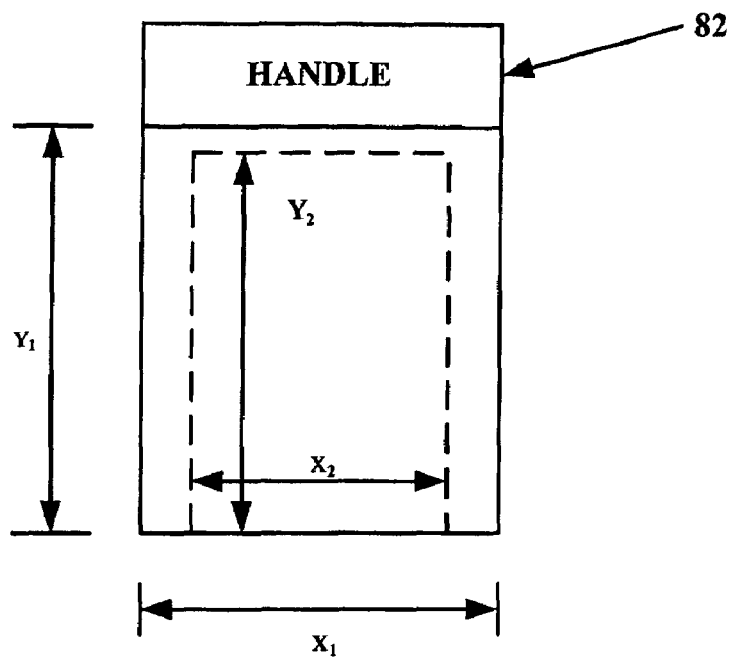
FIGS. 10a and 10b illustrate a laminated membrane article of the present invention.
Figure 10B:
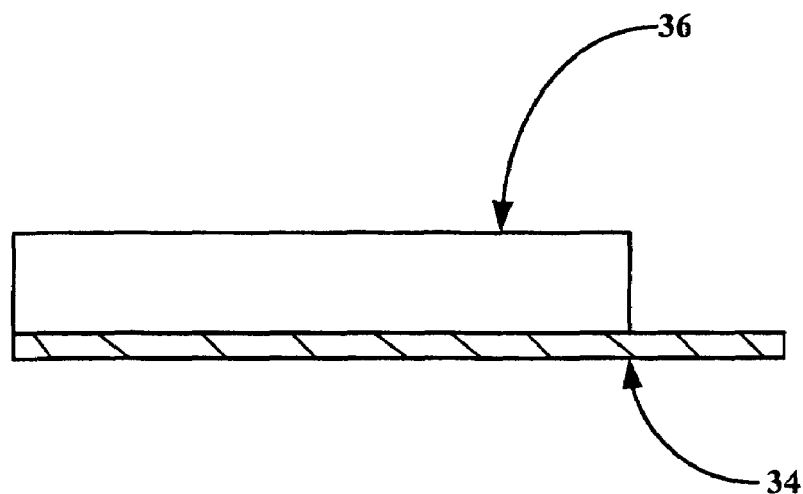

Actual range values may vary according to the specific fluids and surfaces used. In the previous example, values reflected DI water with Superfrost™ glass and Teflon® Plumbers Tape Military Grade. While actual values might vary accordingly, low, middle, and high volume ranges are thus characterized providing specific design spaces for consideration. In the case of a slide, the targeted "treatment zone" is provided by a contact area. The contact area is determined by the opposition of first and second substrates (substrate and slide surfaces) when brought together involving an intermediary fluid. If one of the two surfaces terminates at a particular boundary, the fluid boundary essentially co-terminates at this boundary as well-in effect, we have a "controlling surface" defining the shape of the thin fluid body. Conversely, the alternate surface may extend without effect on the fluid shape since it is non-controlling. Either surface can be controlling. This is illustrated in FIGS. 10a and 10b. This is important because the boundaries of the thin fluid layer can be thus managed while the physical dimensions of one of the surfaces (at a time, per boundary) can be relaxed allowing for, e.g., non-treatment of the label area of the glass slide and oversizing of the substrate, e.g., for handling purposes, as will be discussed below.

Figure 8A:
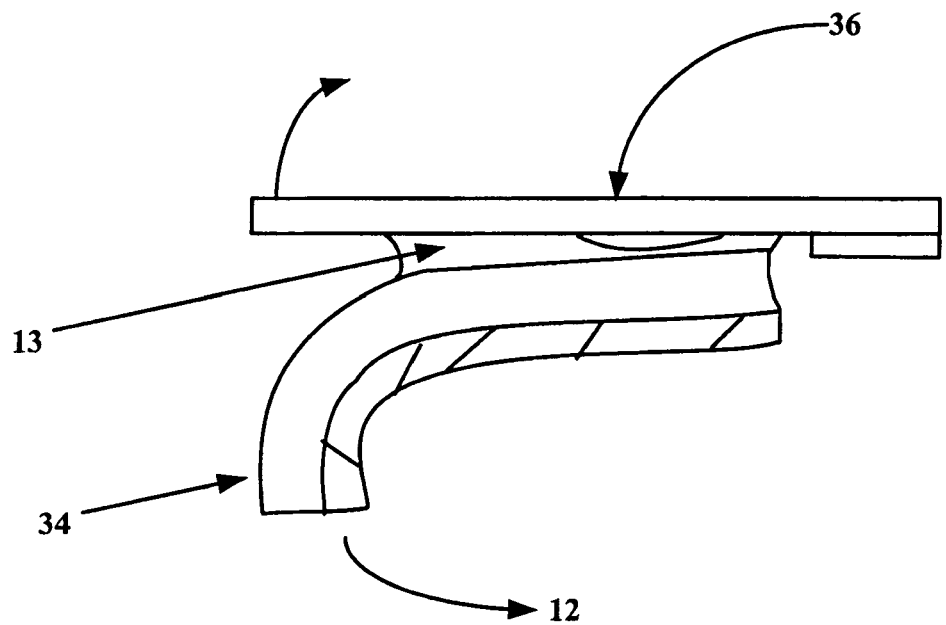
FIGS. 8a and 8b illustrate manual separation of the slide from a substrate in accordance with the present invention.
Figure 8B:
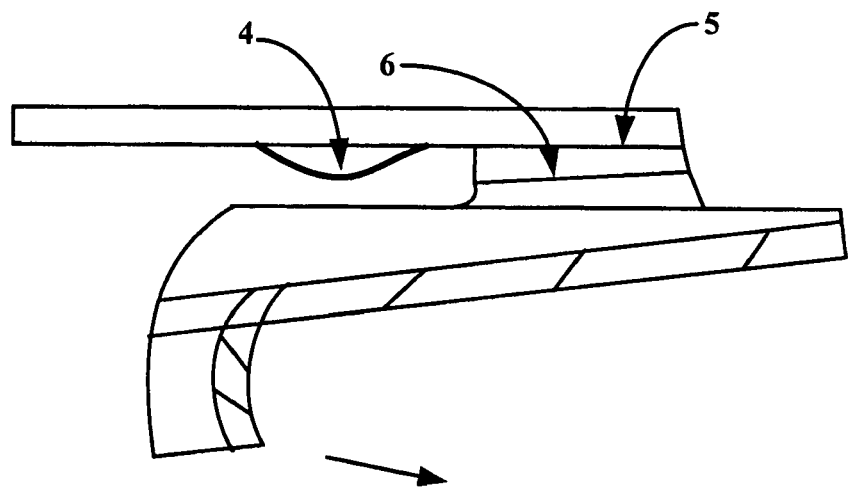
Figure 9A:
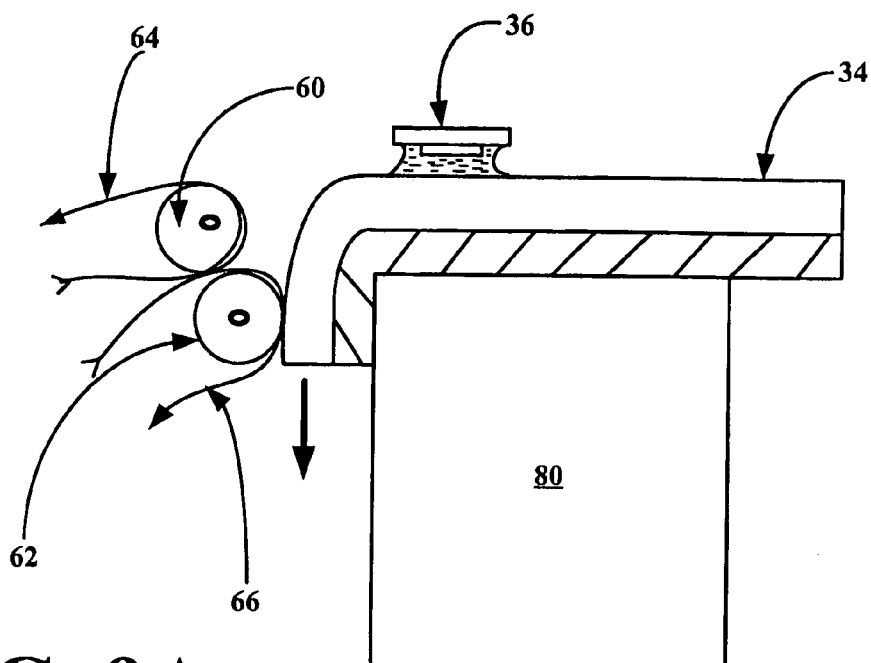
FIGS. 9a and 9b illustrate mechanical assisted separation of the slide from a substrate in accordance with the present invention.
Figure 9B:
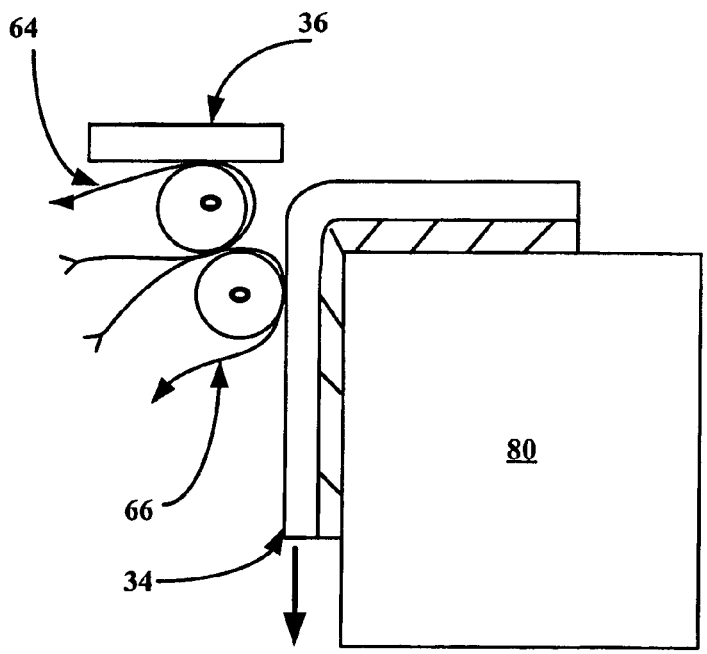

The ability of the present invention to eliminate gas bubbles and spread a relatively small liquid volume across a relatively large surface area while advantageous, also may present a technical challenge in subsequent separation of the specimen slide from the substrate due to significant liquid adhesive forces between the specimen slide and the substrate especially at lower volumes. Thus, the present invention, in another aspect, provides a system for facilitating this separation. FIGS. 7, 8a and 8b illustrate separation of the glass specimen slide 36 from the substrate 34 in a manner that deals with the significant liquid tension that results between the specimen slide 36 and the substrate 34, by "peeling" of the flexible substrate 34 away from the specimen slide 36. Various manual and/or mechanical means for lying down and peeling back the flexible substrate 34 onto and from the specimen slide 36 are envisioned. FIGS. 8a and 8b illustrate manual separation and FIGS. 9a and 9b illustrate an embodiment wherein belt drives 60, 62 actuate both peeling and separation of the flexible substrate 34 from the specimen slide 36 while simultaneously damping off and wicking away spent fluid volumes on absorbent belts 64, 66 carried on the belt drives 60, 62.

The first substrate comprises a relatively fluid-impermeable element. Typically this substrate is glass, plastic or metal that holds the biological substrate sample. The second substrate comprises a relatively flexible gas permeable element, and includes the Gortex® membranes mentioned above.

The invention will be further illustrated by the following examples which are intended to illustrate the invention and not limit it in any way.

Materials List

Substrate: Paraffin-embedded tonsil sections mounted on precleaned Superfrost® Plus microscope slides, 25×75×1 mm (Erie Scientific Company), were air dried and stored in a slide box for several days prior to treatments.

Fluidic device-contacting membrane element: Metricelg®47 mm disks 0.1 um porosity polypropylene, Pall Corporation, East Hills, N.Y. P/N M5P4047.

Fluidic device-backing element: Transparent single side adhesive silicone sheeting 0.020" thickness, McMaster-Carr Supply Company P/N R700549PK.

Fluidic device construct: From silicone sheeting were cut out a ~2.7×~6.5 cm rectangular section. The adhesive backing material was removed from all but the last ~2 cm of the sections—this end serves as a handle for the final device. Over the exposed adhesive, a 47 mm disk was oriented and adhered. The laminate was then trimmed to remove excess overhang materials. Because of the curvature of the disk, the silicone sheeting was trimmed with a slight curving of the rectangular corners to maximize available contacting area for treatment. (See FIGS. 10a). Final area of the membrane surface is ~2.7×4.4 cm. The same device construction was used through all aqueous steps involved through immunohistochemical staining (IHC).

Solvent fluidic device: Since non-polar solvents wet out the above described device, another material was used in treating the sample through the depar and dehydration operations. ~7 cm length of Tissue-Tek® SCA™ coverslipping film (Sakura Finetek USA, Torrance, Calif., P/N 4770) was used. One side contains adhesive—the non-adhesive side was used to spread solvents for treating the sample. The same material was used through all non-polar steps in depar and dehydration.

Coverslipping: A 5.2 cm length of the same coverslipping material was used to coverslip the sample in the final operation.

Wicking Pads: Two were used, one for absorbing aqueous solutions, one for non-polar solvent collection. Gel Blot paper P/N GB003 from Schleicher & Schuell Bioscience, Inc., Keene, N.H., was used, cut to 3×6 cm sections. A small piece of Scotch ®Tape (3M Company, St. Paul, Minn.) was taped to the last ~0.5 cm ends and then adhered back onto itself to act as a handle. For the aqueous pad: it was soaked in Reaction Buffer Concentrate (10×) diluted to 1:10 in deionized water (Ventana Medical Systems, Inc., Cat # 950-300). Upon soaking, excess was squeezed out by mild compression of the wetted pad. The objective was to have a moist absorbent pad for effective wicking. The majority of the originally absorbed solution was squeezed out such that the pad was "damp" rather than "soaked".

Staging area: A 5×7.5×9.5 cm aluminum block 80 was used as a stage for placement of the slide and articles during treatment [FIG. 11].

Tools: a VWR brand pipette 0.010-0.100 mL (VWR International, Inc., West Chester, Pa.) range was used for collecting and dispensing precise volumes of reagent.

Reagents: Confirm™ Anti-CD34 (Clone QBEnd/10) Ventana Medical Systems, Inc. cat# 790-2927 was used as the primary antibody designed to stain vascular endothelial cells. The secondary antibody was Universal Secondary Antibody™ Ventana Medical Systems, Inc., P/N 760-4205 Ventana Medical Systems, Inc. The other reagents were from DAB MAP™ Kit cat# 760-124 Ventana Medical Systems, Inc. The Blocker D reagent was not used in this example in order to demonstrate just how bad the background might get as a result of processing without the benefit of a blocker. Each reagent (~0.100 ml) was transferred into 0.2 ml microfuge tubes for use.

Method

Figure 11:
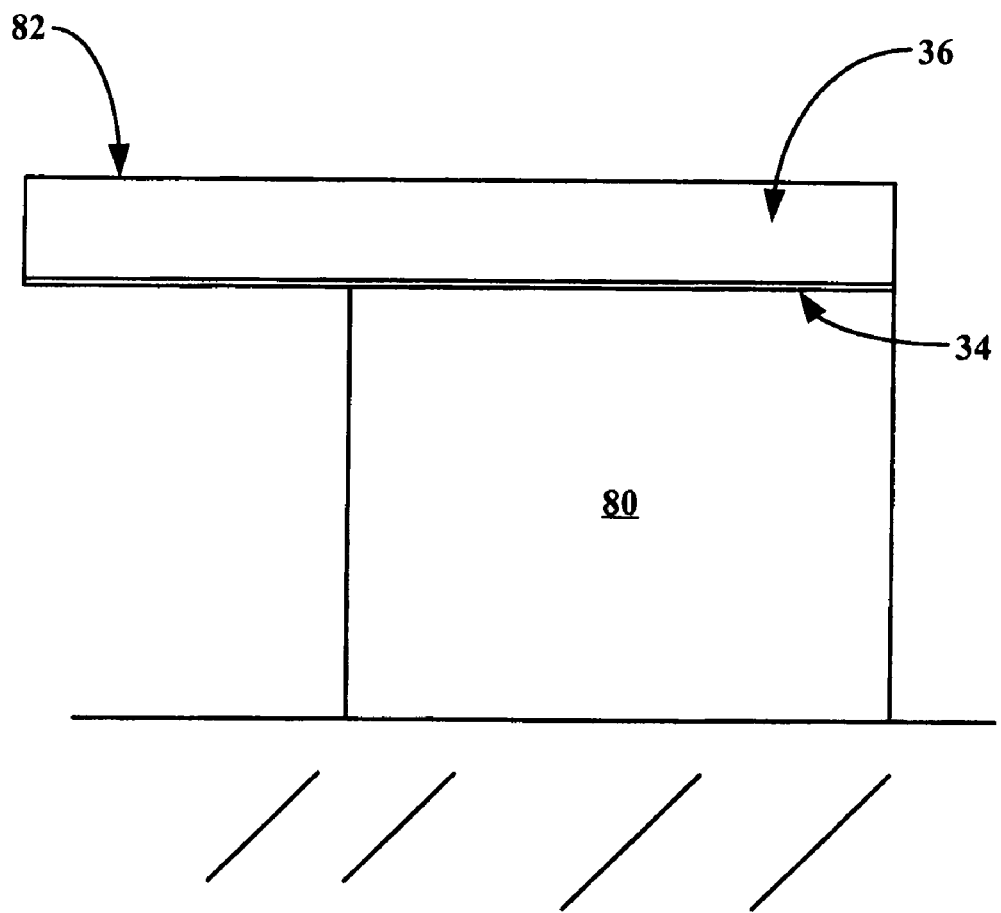
FIG. 11 illustrates a bench system made in accordance with the present invention.
Figure 12:
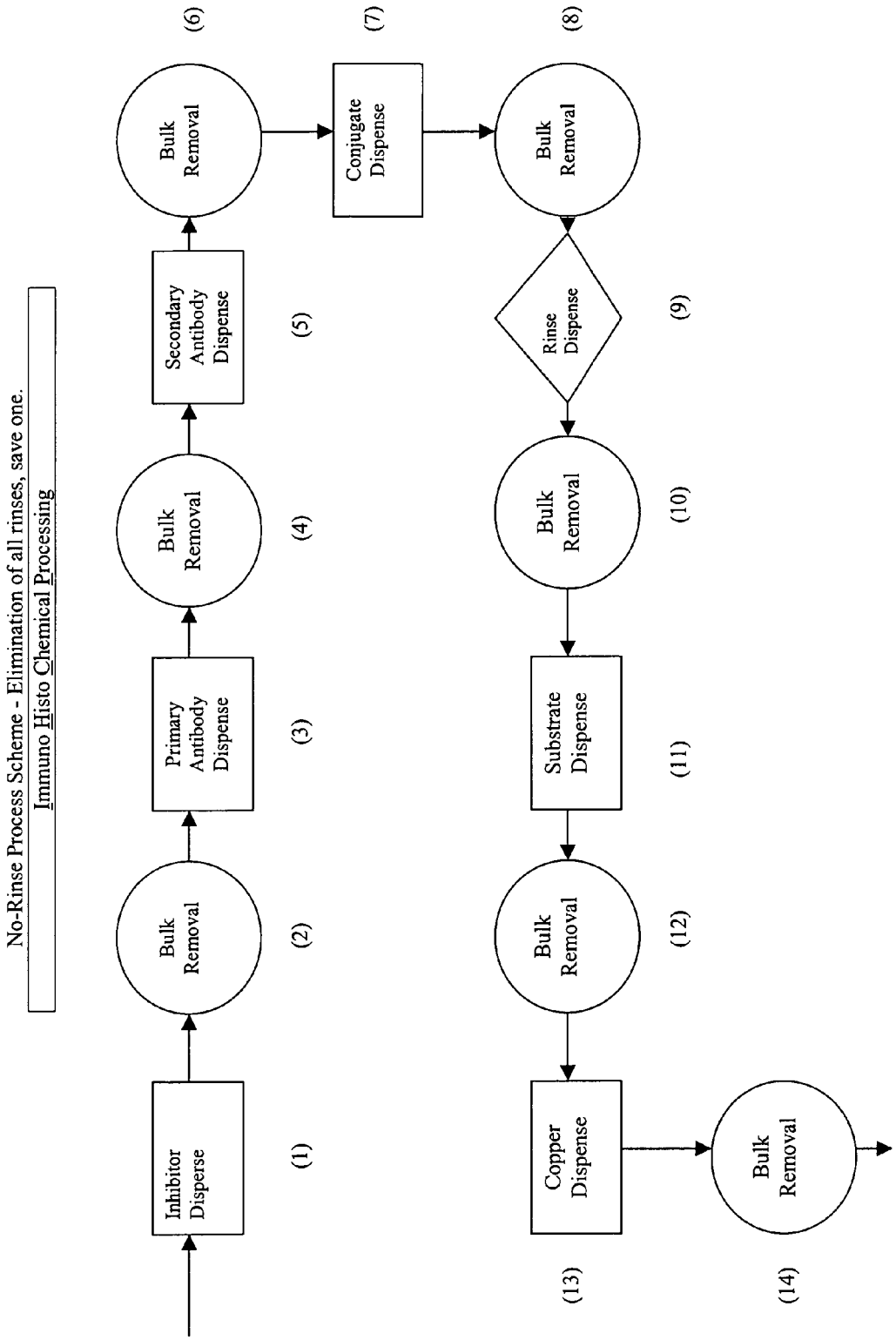
FIG. 12 diagrammatically illustrates a process scheme of one embodiment of the invention.

Staging: Referring to FIGS. 11 and 12, set up flat top aluminum block or stage 80 on end on lab bench. There is an orientation option—either the glass slide may be placed first onto the block and the membrane article with fluid sandwiched in between placed on top, or, the membrane article may be placed down first and the glass slide placed on top. In terms of treatment, it has been found to be immaterial which orientation is selected. Since a fluid drop is dispensed as an intermediary step, it was found generally for manual application that it was more convenient to first place the membrane down, followed by the fluid dispense, followed by opposition (sandwiching) of the glass slide on top. This also had the added advantage in that one could visually observe fluidic behavior through the backside of the transparent glass from a top view. With low volume applications, over expression of fluid at the boundaries is of little to no concern since there is so little excess and since the fluid behaves in a highly viscous manner facilitating fluid placement control. At higher volume applications, however, fluid may tend to over-express at the boundaries and excess management may become a concern. With over-expression, care should be taken with respect to stage design such that no wicking or contacting surfaces from the stage are near any fluid boundaries (e.g., use a stage slightly smaller in size than the mounted substrate). Such a design provides for a robust processing area where a wide range of volumes may be exercised. In the present case, the membrane article was placed flat and more or less central onto the block such that when the slide was then placed down, the label end 82 of the slide overhung the edge of the stage. (See FIG. 11). This allowed for ready access and handling of the slide. Picking up the slide also picked up the membrane article "adhered" via the fluid to the slide. This "sandwich" could be safely manipulated in space—turned around and upside down—without disruption of the elements, fluid, or their relative dispositions.

Contacting Area: The membrane surface area is ~2.7×4.4 cm. The designated glass slide treatment area is 2.5x~5.0 cm. The glass slide width (2.5 cm) dictates the width of the contacting area whereas the membrane length (4.4 cm) dictates the length of the contacting area. In other words, the membrane overhangs the glass in the width dimension while the glass overhangs the membrane in the length dimension. (See FIGS. 10*a* and 10*b*). The resulting contact area is thus 2.5×4.4=11 cm$^2$. The tissue section was placed well within the treatment area. 0.020 ml fluid volumes were used for all fluid applications, since this was previously determined to be sufficient for both coverage and burping purposes. This resulted in a 0.020/11 or 0.0018 ml per cm$^2$ "fluidic operational" value. This is at the low volumetric end or viscous regime. High viscosity was clearly observed, but there was not a single incident of failure or retardation of burping observed at any step.

IHC treatment—dispenses: In order to perform a proper immunohistochemical stain, a specific series of reagents must be applied for specified time exposures. Concentrations are established by the kit manufacturer. It was decided to use all the reagents in the full concentrated form without dilution. This provided for acceleration of treatment such that a standard 2 minute exposure time could be used for every step. Different exposure times were not tested nor optimized beyond this setting. 0.020 ml fluid volumes were applied to the slide for each dispense. It was also decided to eliminate all rinse dispenses with the exception of one applied after the SA-HRP treatment. An unexpected finding was that rinse applications were not necessary at any of the reagent steps with the one exception—as long as the bulk of the reagent volumes could be removed by other means. For the singular rinse step, Reaction Buffer concentrated (10×) diluted 1:10 was used (0.020 ml). Placement of the dispensed volume was not critical as the act of sandwiching spreads the fluid evenly between the opposing surfaces. This is significant in that with automation, instrumentation design may be relaxed on this point. Dispenses were generally placed somewhere centrally onto the fluidic article. The first dispense involved Inhibitor D. It was found that 0.020 ml barely covered the full contact area. Subsequent applications of the other reagents exhibited no difficulty with coverage, on the other hand. It is possible that the first use of a virgin membrane surface is sub-optimal and not preferred. Thus, a pre-conditioning where the membrane is exposed to protein absorption may enhance spreadability in subsequent steps.

Treatment Sequence:
1) Inhibitor, 2) Anti-CD34, 3) Universal Secondary Antibody, 4) SA-HRP, 5) Reaction Buffer Rinse, 6) DAB+DAB H202, 7) Copper.

In step 6, two reagents were applied together. In the present case, 0.020 ml of DAB was pre-mixed with 0.020 ml of DAB H202 just prior to slide dispense. Only 0.020 ml of the mix was applied.

IHC treatment—fluid removal: After each treatment of 2 minute, the sandwich was picked up into the air by the glass slide label end, the handle end of the fluidic article was grabbed, and the membrane peeled away from the slide surface. The fluidic device was then returned to the aluminum block or stage, the moistened blotting paper was placed on top, and then the glass slide was placed on top of the blotting paper. Slight pressure was applied to the top of this new sandwich such that excess fluids at both the fluidic and slide surfaces could be readily absorbed into both blotting paper surfaces simultaneously. Total time to perform such a wicking operation was between 10 and 20 seconds, largely depending upon manual dexterity. Actual wicking time was probably—less than—5 seconds.

Solvent deparaffinization treatment: A specific series of solvent exposures were applied in order to effectively remove paraffin while returning tissue back to an aqueous state. The treatment operations were essentially the same as those described for the IHC operations with a few notable differences. The glass slide was placed face up onto the stage with the fluidic article placed on top sandwiching the fluids—upside down with respect to aqueous processing. The fluidic article (Sakura coverslip plastic strip) is quite thin, so it was easier to prevent fluids from exceeding their boundaries with the glass slide sitting with its wetted surface 1 mm above the stage surface. Further, the plastic is transparent so visualization was sufficient. The most significant difference is that the fluidic device in this instance is non-burpable. Sliding the plastic strip back and forth over the "fluid bearing" provided adequate exposure of the tissue to the solvents in spite of entrapped gas pockets. This method is an important alternative and unique method for assuring full coverage treatment, one that mitigates the effect of entrapped gas pockets.

Since fluids are directly applied to the treatment area, it is important to immediately sandwich the fluidic device with the slide for homogeneous treatment. Solvents in all cases were applied for only ~10 seconds per application. Wicking was performed the same way as in the IHC aqueous case, except that a separate wicking pad (dry) was used for collecting excess non-polar solvents. 0.020 ml volumes were used per application.

Treatment Sequence:
1) Xylene (repeated 3×), 2) 100% ETOH (repeated 2×), 3) Reaction Buffer (just once)

At the end of treatment (while in step 3), tissue was parked and therefore "soaked" in Reaction Buffer for several minutes as the IHC process was being set up.

Dehydration Treatment: Essentially the same operations as the deparaffinization were applied, just in reverse. The same solvent wicking pad was used.

Treatment Sequence:
1) 100% ETOH (repeated 3×), 2) Xylene (one time), 3) Xylene+Sakura coverglass.

It was observed that 0.020 ml was an insufficient volume for the coverglass step 3. An additional 0.020 ml was added around the finished coverglass to displace the air and supplement the originally applied volume.

There was no intermediary step between final treatment of Copper reagent wicking during the IHC operation and dehydration—the sample went straight from IHC to solvent applications.

Final Results and Advantages:

Total process time from wax to coverglass=20 minutes. This is very fast where analogous process of using conventional prior art techniques would take ~90 minutes just for the depar+IHC operations alone.

Total fluids consumption: 0.160 ml aqueous; 0.120 Xylene; 0.100 ETOH. This is ~1000× reduction compared to conventional processes.

Total fluids stream waste: none; only 2 moist wicking membranes.

80% reduction in expensive reagent volumes (0.020 ml treatment compared to 0.100 ml on the BenchMark, per reagent).

Elimination of all but one rinsing step. More economical; faster.

Elimination of all mixing requirements; no mixing overhead

Both stain and background are acceptable.

The elimination of holding steps between depar, IHC, dehydration, and coverslipping operations—a continuous process from deparaffinization through coverglassing.

The ability to operate with extremely small quantities of liquid reagent provides several features and advantages over the prior art. For one, stains and reagents may be used in concentrated, undiluted form. As a result, liquid volume may be significantly reduced, and wash or rinse volume also may be significantly reduced. Also, depending on the nature of the reagent or stain and subsequent operations, it may be possible to eliminate one or more wash or rinse steps. This latter feature and advantage to the present invention is quite unexpected and contrary to current practices of the prior art in which heretofore it has been accepted that rinsing between applications of subsequent reagents is inherent to the processes involved in the proper (i.e., clean) staining of slides. By employing a hydrophobic flexible substrate 32 in accordance with the present invention, it is possible to displace spent reagent or stain by other means than rinsing. In other words, it has been discovered that reagent displacement alone sometimes may be sufficient for processing slides through staining. Therefore, in accordance with another aspect of the present invention alternative displacement means can be provided which eliminates the need for any rinsing operations. For example, spent stain or reagent may be removed by wicking using a blotting paper or cloth such as Gel Blot Paper (GB002or GB003, available from Schleicher & Schuell Bio-Science, Inc.) (see FIGS. 9a-9b), and the slides further treated without any rinsing. Alternatively, the spent stain or reagent may be removed by air knifing or spinning (see FIG. 13b). This has the advantage of resulting in a reduction in total fluid volumes of ~1000× compared to presently commercially available systems. No liquid waste stream need be generated; the only waste involved are small aqueous-moist and non-polar-moist wicking pads derived from reagent collection. In other words, the present invention permits reduction in liquid consumables and waste by elimination of rinsing or washing between one or more staining or reagent steps.

The ability to satisfactorily conduct one or more reagent steps without intervening wash or rinse is unexpected and contrary to the currently accepted legacy coming from the old "bucket chemistry" days, ingrained dogma, and general heightened concern surrounding background, carry-over, and the ideal of chemical isolation. With pressure towards volume reduction, process acceleration, and improved instrument reliability, processes such as rinsing are coming under greater scrutiny. The present invention provides an optimal method for auto-staining slides that eliminates many of the disadvantages inherent in prior art systems.

Figure 13A:
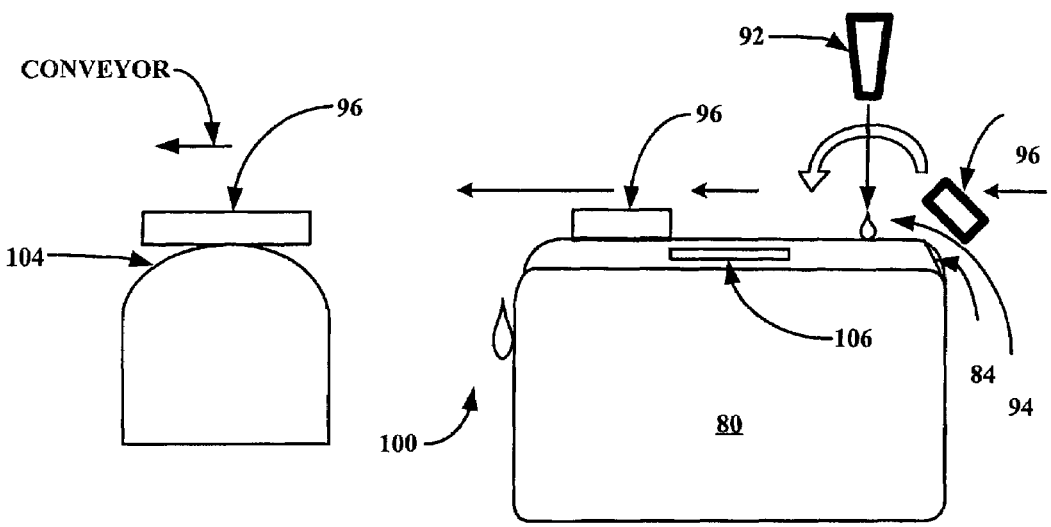
FIGS. 13a and 13b are views similar to FIGS. 9a and 9b of alternative systems made in accordance with the present invention.
Figure 13B:
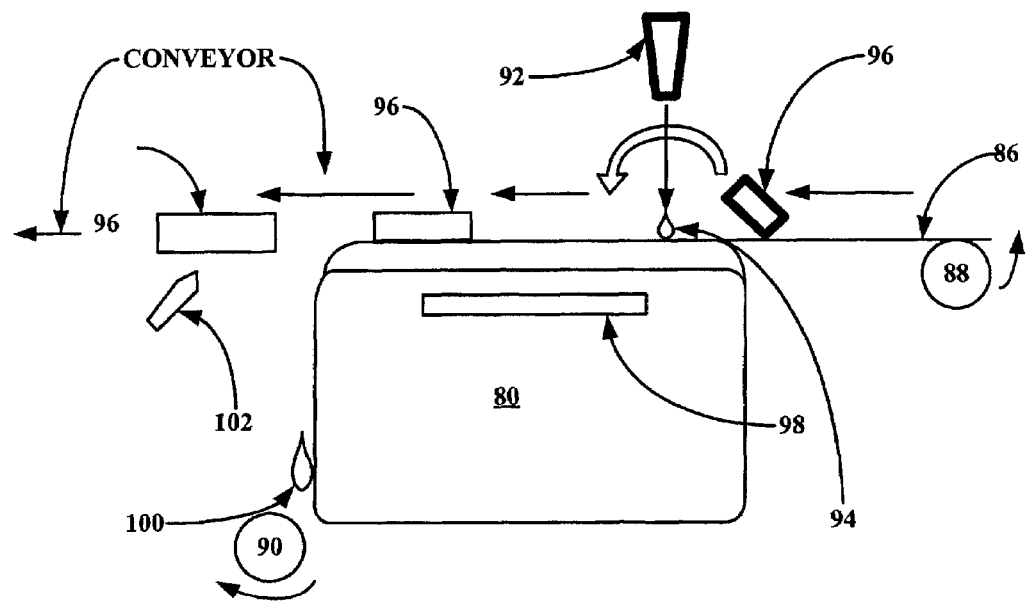

Referring to FIGS. 13a and 13b there are illustrated yet other alternative embodiments of the present invention which permit control of slide entry angle and motion to discourage bubble entrapment and mitigation of unintended bubble entrapment. In FIG. 13a the system includes a base station 80 upon which a replaceable surface element 84 is fitted. Element 84 may comprise a fixed article, such as an injection molded plastic plate, that can be periodically replaced with a new piece. In this manner, a well-controlled fluidic surface quality may be managed. Alternatively, as shown in FIG. 13(b) the surface element may comprise a membrane sheet 86 threaded and held tautly between a feed roller 88 and a take-up roller 90 which permits fresh membrane to be advanced, as necessary, and thus provide fresh surface assuring well-controlled fluidic surface quality. A dispenser 92 dispenses a fluid drop 94 of known volume onto the right entry side of element 84 or 86 as the case may be. A slide 96 is conveyed (details of the conveyance means not shown for the sake of clarity) initially at an angle so as to contact the fluid drop 94 and then oriented in parallel with the surface plane of element 84 or 86 as the case may be as it is further conveyed to the left. Conveyance of slide 96 may be independent of conveyance of element 84 or 86, as the case may be. Keeping conveyance independent of the relative motion of slide 96 with respect to element 84 or 86 as the case may be in combination with angled contacting of the slide with droplet 94 and motion to parallel orientation with element 84 or 86 as the case may be ensures essentially bubble-free fluid spreading and coverage within the resulting capillary gap. The capillary gap is defined as any continuous opposition of slide 96 with element 84 or 86 as the case may be in which fluid can fill. Slide 96 is conveyed across the surface of the device reaching the far side at left. The speed of conveyance controls the time of slide 96 surface exposure (incubation) to capillary gap fluid. Throughput may be increased by increasing the length of the base 80 and/or by incorporating heating means 98 or 106 into the base 80. With heating the speed of conveyance may be increased in order to maintain equivalent incubation effect thereby increasing the capacity to process more slides. As slide 96 is further conveyed, it is incrementally removed from the device. Most fluid tends to remain within the diminishing remaining capillary gap. Upon conveyance beyond the boundary of element 84 or 86 as the case may be, the majority of the fluid spills down the side of device as fluid droplets 100 leaving treated surface of the slide 96 largely free of excessive residual fluid. Slide 96 may be further conveyed to another location and treated to remove additional surface fluid, if needed, for example by an air knife 102 or absorbent porous membrane surface element 104 treatment. Additional like base stations and dispensers, etc., may be used in series in order to affect a series of chemical surface treatments in the same manner.

Also, a heater element 98 or 106 may be incorporated into element 84 or the entire system may be placed within a chamber with controlled heating capabilities.

It is thus seen the present invention provides significant methods and systems for staining or incubating micro volumes on substrate surfaces. Fluid volumes on the scale of 20-50 ul can be spread as thin layers over large surface glass slide areas (12.5 cm² area>1.6-4.0 ul/cm²). The fluid on the slide may be maintained in a non-sealed manner such that a specified treatment area is contacted for appropriate fluidic exposure. Maintenance of a continuous thin aqueous layers without disruption is a recognized challenge. The present invention provides a system for spreading a small liquid volume across a large surface area while providing a regulated passive escape of trapped or formative gas pockets while avoiding significant evaporative loss.

The invention has other advantages. With direct concentrated reagent application, processes may be accelerated and the requirement of mixing reagent with a diluent eliminated. Application of concentrated reagents also means that liquid volume dispense precision may be relaxed, since concentration, not volume, becomes the controlling factor.

The invention is useful in providing well-controlled serial incubations of specific chemistries. Elimination/reduction of heavy rinsing in combination with small reagent volume applications suggests new architectural opportunities, such as miniaturization, system integration, and elimination of complex sub-systems (e.g., liquid waste management system). For example, at a higher architecture level multiple slide stations may be configured for high throughput by virtue of parallel processing. While the present system does require the added steps of applying and then peeling a membrane article from a slide surface, the "cost" of these additional steps is more than offset by several gains including speed, reduction in fluid volume consumption, and reduction/elimination in fluid volume wastes.

The invention provides other advantages. For example, most or all of an entire tissue testing system could be integrated into a single miniaturized station. For example, 7 reagents plus 2 rinses could be packaged as separate wells on a single disposable "micro-fluidic card" to provide IHC staining of a single slide. A micro fluidic approach allows for the possibility of integrating individualized slide fluidics permitting a different instrument design space. The entire station could be the size of, e.g., a small hand-held camera. Plumbing and large scale mechanics could be eliminated. Miniaturization and integration offer simplicity, design for quality control, robustness, and various types of cost reductions. Modules may be ganged for higher throughput while providing true parallel processing means.

While the foregoing invention has been described largely in connection with aqueous-based fluids, the invention advantageously also may be used with non-aqueous fluids. In such case, there would be no need to employ a hydrophobic element as the second substrate as described in the foregoing. Thus, many variations are possible which remain within the concept and scope of the invention.

The invention claimed is:

1. An apparatus for treating a biological sample with a liquid reagent comprising first and second substrates having facing surfaces defining a space therebetween in which said biological sample may be treated with said liquid reagent, wherein said first substrate comprises a relatively rigid fluid impermeable element for supporting said biological sample while said second substrate comprises a relatively flexible gas permeable element, said apparatus further including a device for moving and separating at least one of said first and second substrates relative to the other without displacing said biological sample from said relatively rigid substrate.

2. The apparatus of claim 1, wherein said device for separating includes porous material for removing liquid reagent from one or both of said first and second substrates.

3. The apparatus of claim 1, further including a heater for heating at least one of said first and second substrates.

4. An apparatus of claim 1, and further including a conveyor for moving said first substrate relative to said second substrate.

5. An apparatus of claim 4 wherein said conveyor is adapted to move said first substrate at an angle to vertical.

6. The apparatus of claim 1, wherein said second substrate comprises an elongate flexible tape.

7. The apparatus of claim 6, wherein said elongate flexible tape is threaded between a feed roller and a take up roller.

8. The apparatus of claim 1, and further including an air knife.

9. The apparatus of claim 1, and further includes a blotting device.

10. The apparatus of claim 1, wherein said second substrate comprises a gas permeable hydrophobic element.

11. The apparatus of claim 10, wherein said gas permeable hydrophobic element comprises a gas permeable porous membrane.

12. The apparatus of claim 11, wherein said gas permeable porous membrane is laminated to a liquid impermeable backing element.

13. The apparatus of claim 11, wherein said gas permeable porous membrane is disposed in contact with a liquid impermeable substrate.

14. A method for treating a biological sample with a liquid reagent comprising the steps of providing an apparatus as claimed in claim 1, providing said sample in liquid reagent in said space defined between said facing surfaces, pressing said substrates together to reduce the space therebetween and expel gas trapped therebetween and separating said substrates.

15. The method of claim 14 and including the step of removing excess reagent from one or both of said substrates by contact with a porous material.

16. The apparatus of claim 1, wherein said specimen is carried on said first substrate.

17. The apparatus of claim 16, wherein said first substrate comprises a glass slide.

18. The apparatus of claim 17, wherein said biological specimen comprises a sectioned tissue sample carried on said slide.

19. The apparatus of claim 17, wherein said biological sample comprises a cytological prep carried on said slide.

20. The apparatus of claim 17, wherein said biological sample comprises a tissue sample array carried on said slide.

21. The apparatus of claim 17, wherein said biological sample comprises a DNA micro array carried on said slide.

22. The apparatus of claim 17, wherein said biological sample comprises a protein micro array carried on said slide.

23. The apparatus of claim 1, wherein said second substrate comprises a gas permeable hydrophobic porous flexible membrane.

24. The apparatus of claim 23, wherein said gas permeable hydrophobic porous flexible membrane comprises a polytetrafluoroethylene tape or sheet.

25. The apparatus of claim 23, wherein said gas permeable hydrophobic porous flexible membrane comprises a microporous semipermeable tape or sheet.

26. The apparatus of claim 23, wherein said gas permeable hydrophobic porous flexible membrane is backed by a liquid impermeable element.

27. The apparatus of claim 26, wherein said gas permeable hydrophobic porous flexible membrane is laminated to a liquid impermeable backing element.

28. The apparatus of claim 26, wherein said gas permeable hydrophobic porous flexible membrane is disposed in contact with a liquid impermeable substrate.

29. The apparatus of claim 1, wherein said liquid reagent comprises a biological stain or biological reagent.

30. The apparatus of claim 1, wherein said liquid reagent comprises an aqueous based solution.

31. The apparatus of claim 1, wherein said liquid reagent is spread substantially uniformly between said facing surfaces.

32. The apparatus of claim 1, wherein said liquid reagent is substantially free of gas bubbles.

33. The apparatus of claim 1, wherein said liquid reagent is in the form of a liquid film having a film thickness of about 7-360 um.

34. The apparatus of claim 1, wherein said liquid reagent has a volume of about 100-300 microliters.

35. The apparatus of claim 34, wherein the liquid reagent has a volume of about 5-50 microliters.

36. The apparatus of claim 35, wherein the liquid reagent has a volume of about 20 microliters.

37. An apparatus according to claim 1, wherein at least one of said first and second substances is rectangular in plan.

38. An apparatus according to claim 1, wherein both said first and second substrates are rectangular in plan.

39. The apparatus of claim 1 wherein said space comprises an aqueous reagent and defines an open-sided reaction chamber.

40. The apparatus of claim 1 wherein said gas permeable element is backed by a substantially non-permeable flexible membrane or coating such that vapor pressure between said liquid reagent and atmosphere is mediated laterally through said gas permeable membrane.

* * * * *

UNITED STATES PATENT AND TRADEMARK OFFICE
CERTIFICATE OF CORRECTION

PATENT NO. : 7,615,371 B2
APPLICATION NO. : 11/016407
DATED : November 10, 2009
INVENTOR(S) : Brian H. Kram It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 948 days.

Signed and Sealed this

Nineteenth Day of October, 2010

David J. Kappos
*Director of the United States Patent and Trademark Office*